(12) United States Patent
Fukuda

(10) Patent No.: US 9,885,673 B2
(45) Date of Patent: Feb. 6, 2018

(54) METHOD AND APPARATUS FOR DETECTING DEFECT IN TRANSPARENT BODY

(71) Applicant: MITUTOYO CORPORATION, Kawasaki-shi, Kanagawa (JP)

(72) Inventor: Shinji Fukuda, Tokyo (JP)

(73) Assignee: MITUTOYO CORPORATION, Kawasaki-shi (JP)

( * ) Notice: Subject to any disclaimer, the term of this patent is extended or adjusted under 35 U.S.C. 154(b) by 0 days.

(21) Appl. No.: 15/472,870

(22) Filed: Mar. 29, 2017

(65) Prior Publication Data

US 2017/0307546 A1    Oct. 26, 2017

(30) Foreign Application Priority Data

Apr. 26, 2016  (JP) ................................. 2016-088568

(51) Int. Cl.
| | | |
|---|---|---|
| *G01N 21/00* | (2006.01) | |
| *G01N 21/958* | (2006.01) | |
| *G01N 21/88* | (2006.01) | |

(52) U.S. Cl.
CPC ....... *G01N 21/958* (2013.01); *G01N 21/8806* (2013.01); *G01N 21/88* (2013.01)

(58) Field of Classification Search
CPC .. G01N 21/958; G01N 21/9583; G01N 21/88; G01N 21/8806

USPC ...................... 356/239.7, 239.8, 237.2–237.3
See application file for complete search history.

(56) References Cited

U.S. PATENT DOCUMENTS

2004/0174519 A1* 9/2004 Gahagan ................ G01N 21/41
356/239.1

FOREIGN PATENT DOCUMENTS

| | | |
|---|---|---|
| EP | 2253949 A1 | 11/2010 |
| JP | H09-138115 A | 5/1997 |
| JP | 2002-131041 A | 5/2002 |
| JP | 2003-156326 A | 5/2003 |
| JP | 4162426 B2 | 10/2008 |
| JP | 4191953 B2 | 12/2008 |
| JP | 5507879 B2 | 5/2014 |
| WO | 2010/133341 A1 | 11/2010 |

* cited by examiner

*Primary Examiner* — Hina F Ayub
(74) *Attorney, Agent, or Firm* — Oliff PLC

(57) ABSTRACT

A quantitative, high-sensitivity examination of defects in a transparent product is realized, using a low-cost and space-saving optical dimension measuring apparatus to carry out measurement in a non-contact manner to avoid damaging the object of inspection and to avoid sensory examination. A transparent body to be examined is disposed between a light emitting unit and a light-receiving unit arranged opposite each other. A change in an optical path caused by a defect in the transparent body is detected based on a change in a light ray emitted from the light emitting unit and being incident on the light-receiving unit after passing through the transparent body and a light-blocking object disposed between the transparent body and the light-receiving unit.

20 Claims, 8 Drawing Sheets

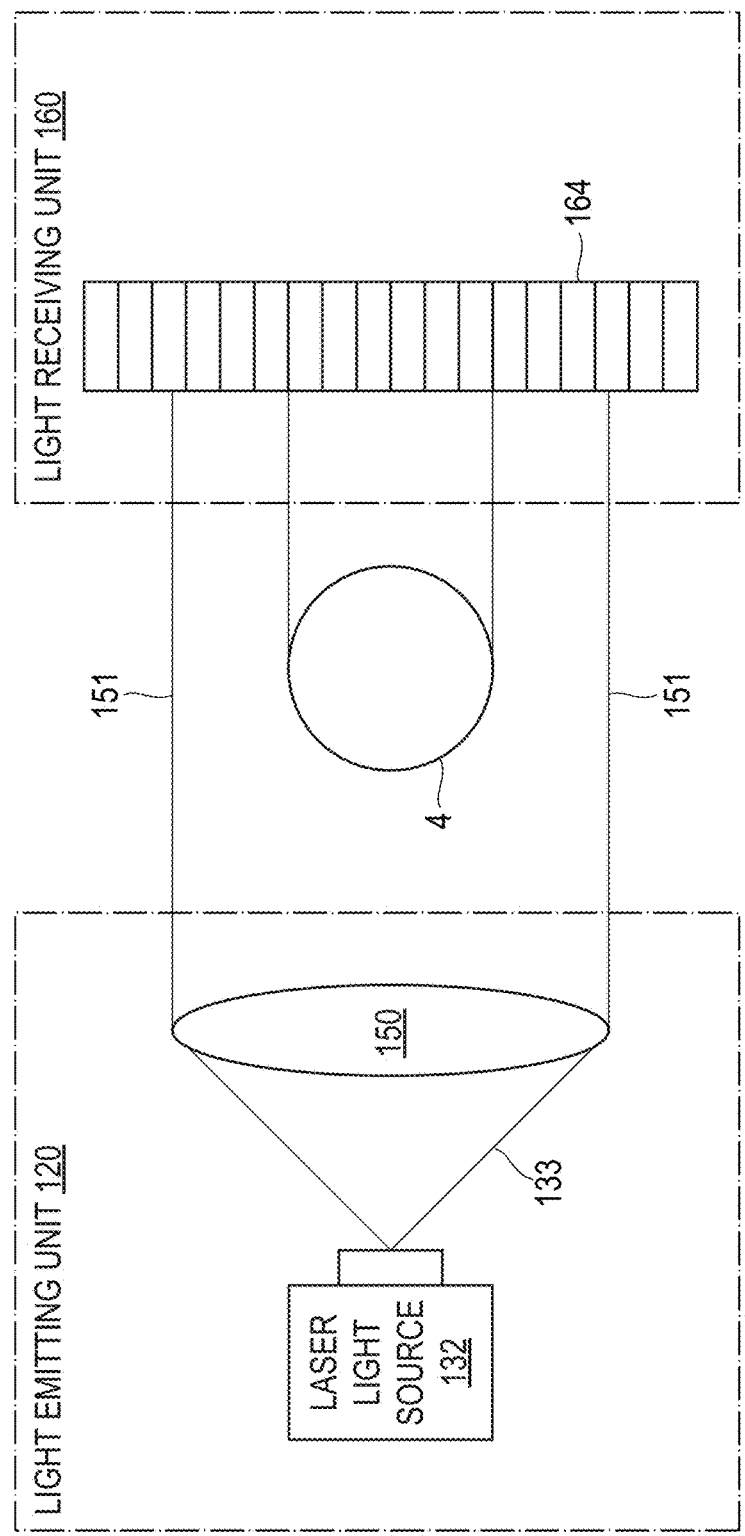

METHOD AND APPARATUS FOR DETECTING DEFECT IN TRANSPARENT BODY

CROSS-REFERENCE TO RELATED APPLICATION

This application claims priority from Japanese Patent Application No. 2016-088568 filed in the Japan Patent Office on Apr. 26, 2016. The entire contents of the prior application are hereby incorporated by reference.

BACKGROUND

The disclosure relates to methods and devices for detecting defects in a transparent body. Particularly, the disclosed embodiments relate to methods and devices for detecting defects in a transparent product such as a glass panel or a lens using an existing optical dimension measuring apparatus.

A technique of using a plurality of light sources, as disclosed in WO 2010/133341A1, for example; a technique of detecting deflection or polarization caused by defects, as disclosed in EP 2253949A1; a technique using a laser interferometer; and a technique of using a contour shape measuring apparatus, such as that disclosed in Japanese Unexamined Patent Application Publication No. 2002-131041A and Japanese Unexamined Patent Application Publication No. 2003-156326A, can all be given as techniques to examine for defects in a glass product, such as a glass panel or a lens, or a transparent plastic product.

Additionally, the laser scanning-type dimension measuring apparatus disclosed in Japanese Patent No. 4162426B and Japanese Patent No. 4191953B (also called a "laser scan micrometer"), and the image sensor-type dimension measuring apparatus disclosed in Japanese Patent No. 5507879B (also called an "image sensor-type micrometer"), which were proposed by the applicant of the present embodiments, are examples of optical dimension measuring apparatus that can be used to measure the outer diameter of a pin gage or a plug gage for measuring the diameter of a hole in an object.

Furthermore, in Japanese Unexamined Patent Application Publication No. H09-138115A, the applicant of the present embodiments has proposed a technique for measuring a transparent body using the aforementioned laser scanning-type dimension measuring apparatus.

SUMMARY

However, the techniques disclosed in WO 2010/133341A1 and EP 2253949A1 must be incorporated into a glass plate manufacturing line, for example, and thus do not conserve space and are expensive.

Meanwhile, when using a laser interferometer, defects are often evaluated by observation using a camera (or by eye). This is merely a sensory examination and is not quantitative. The technique is also expensive, and does not conserve space.

Furthermore, contour shape measuring apparatus carry out contact-based measurement, which is problematic in that the object of examination may be damaged, for example.

The optical dimension measuring apparatus disclosed in Japanese Patent No. 4162426B, Japanese Patent No. 4191953B and Japanese Patent No. 5507879B are capable of non-contact measurement. Such devices have been used to measure transparent bodies in the past, as indicated by Japanese Unexamined Patent Application Publication No. H09-138115A, however, using the devices to examine transparent bodies has not been considered.

Seeking to address the above-described past problems, the present embodiments aim to realize a quantitative, high-sensitivity examination of defects in a transparent product, using a low-cost and space-saving optical dimension measuring apparatus so as to carry out measurement in a non-contact manner to avoid damaging the object of inspection and to avoid a sensory examination.

The disclosed embodiments address the above-described problems using a method for detecting a defect in a transparent body. The method includes: disposing a transparent body to be examined between a light emitting unit and a light-receiving unit arranged opposite each other; and detecting a change in an optical path caused by a defect in the transparent body based on a change in a light ray emitted from the light emitting unit and being incident on the light-receiving unit after passing through the transparent body and a light-blocking object disposed between the transparent body and the light-receiving unit.

According to some embodiments, a laser scanning-type dimension measuring apparatus can be used, in which the light emitting unit scans a laser beam in a measurement direction and the light-receiving unit focuses and detects the scanned laser beam after passing through the transparent body and a light-blocking object.

According to some embodiments, an image sensor-type dimension measuring apparatus can be used, in which the light emitting unit emits a linear light ray and the light-receiving unit receives the linear light ray after passing through the transparent body and a light-blocking object.

According to some embodiments, the light-blocking object can be a pin gage that is moved in the measurement direction.

According to some embodiments, the light-blocking object can be a fixed optical lattice having light and dark areas distributed at intervals smaller than a defect in the transparent body.

According to some embodiments, the transparent body can be a lens.

The present disclosure also provide a device for detecting a defect in a transparent body. The device includes: a light emitting unit; a light-receiving unit disposed opposite from the light emitting unit; a light-blocking object disposed between the light emitting unit and the light-receiving unit; and a controller configured to detect a change in an optical path caused by a defect in a transparent body to be examined based on a change in a light ray emitted from the light emitting unit and incident on the light-receiving unit after passing through the transparent body and the light-blocking object. The device is configured to arrange the transparent body between the light emitting unit and the light-blocking object.

According to some embodiments, the device can be a laser scanning-type in which the light emitting unit includes a scanner that scans a laser beam in a measurement direction and the light-receiving unit includes a condenser that condenses the scanned laser beam after passing through the transparent body and the light-blocking object.

According to some embodiments, the device can be an image sensor type in which the light emitting unit includes an emitter that emits a linear light ray and the light-receiving unit includes a receiver that receives the linear light ray after passing through the transparent body and the light-blocking object.

According to some embodiments, the light-blocking object can be a pin gage that moves in the measurement direction.

According to some embodiments, the light-blocking object can be a fixed optical lattice having light and dark areas distributed at intervals smaller than a defect in the transparent body.

According to some embodiments, the transparent body can be a lens, and the device can include an optical element having a shape corresponding to the shape of the lens.

According to embodiments, it is possible to carry out a quantitative, high-sensitivity examination of defects in a transparent product, using a low-cost and space-saving optical dimension measuring apparatus so as to carry out measurement in a non-contact manner to avoid damaging the object of inspection and to avoid sensory examination.

BRIEF DESCRIPTION OF THE DRAWINGS

FIG. 8 is a block diagram illustrating an example of a configuration of main parts of an image sensor-type optical dimension measuring apparatus that can be used with the disclosed embodiments.

DETAILED DESCRIPTION OF EMBODIMENTS

Hereinafter, embodiments will be described in detail with reference to the drawings. Note that the described embodiments and examples are not intended to be limiting. The constituent elements disclosed in the following embodiments and examples may be combined as appropriate, or selected and used as appropriate.

First, a laser scanning-type dimension measuring apparatus such as that disclosed by the applicant of the present embodiments in Japanese Patent No. 4162426B, Japanese Patent No. 4191953B, or Japanese Unexamined Patent Application Publication No. H09-138115A will be described as an example of an optical dimension measuring apparatus that can be used with the disclosed embodiments.

Figure 1:
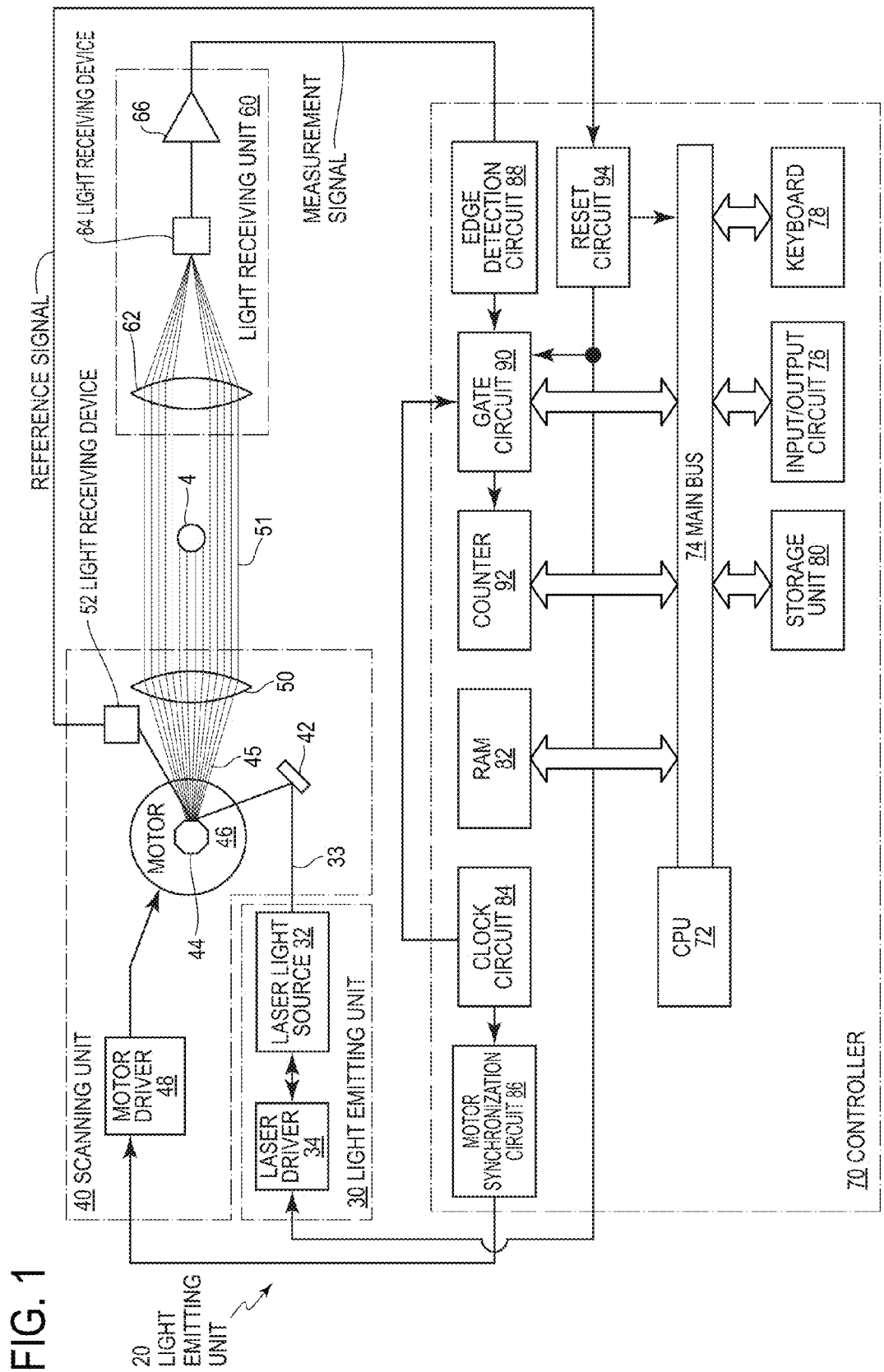
FIG. 1 is a block diagram illustrating an example of a configuration of a laser scanning-type optical dimension measuring apparatus that can be used with the disclosed embodiments.

This laser scanning-type dimension measuring apparatus is configured as illustrated in FIG. 1. A light emitting unit 20 includes: a light-emitting unit 30 including a laser light source (a laser diode LD, for example) 32 that emits a laser beam 33 and a laser driver 34; and a scanning unit 40 constituted of a reflecting mirror 42 that reflects the laser beam 33, a polygon mirror 44 that produces a fan-shaped scanning beam 45, a motor 46 that rotates the polygon mirror 44, a motor driver 48, a collimator lens 50 that changes the fan-shaped scanning beam 45 into a parallel scanning beam 51, and a light receiving device 52 for generating a reference signal outside of a measuring range.

A light-receiving unit 60 receives the parallel scanning beam 51 that has traversed a measurement object 4. The light-receiving unit 60 is constituted of a focusing lens 62 for focusing the parallel scanning beam 51, a measurement signal light receiving device 64, and an amplifier 66.

A controller 70 controls the light emitting unit 20 and the light-receiving unit 60 to obtain a measurement value. The controller 70 is constituted of: a CPU 72; a main bus 74; an input/output circuit 76; a keyboard 78; a storage unit 80; random access memory (RAM) 82; a clock circuit 84; a motor synchronization circuit 86; an edge detection circuit 88 that detects edges from the measurement signal output from the light-receiving unit 60; a gate circuit 90 and a counter 92 for counting clock signals between edges and obtaining a measurement value; and a reset circuit 94 for resetting the measurement in accordance with the reference signal.

In other words, the laser beam 33 emitted from the laser light source 32 is reflected by the reflecting mirror 42, is incident on the polygon mirror 44, and is then changed to the fan-shaped scanning beam 45. The fan-shaped scanning beam 45 is then converted into the parallel scanning beam 51 by the collimator lens 50. The parallel scanning beam 51, which is partially blocked by the measurement object 4 placed within the optical path of the parallel scanning beam 51, is focused by the focusing lens 62, and is then incident on the measurement signal light receiving device 64, which detects the brightness of the beam. The measurement signal output from the light receiving device 64 is amplified by the amplifier 66. Then, the edge detection circuit 88 extracts edge signals indicating borders between light and dark areas, and the measurement signal is then input into the gate circuit 90, which selects an area for measurement.

The light receiving device 52, which is used to generate the reference signal, is provided near the collimator lens 50 for the fan-shaped scanning beam 45. The reference signal obtained by the light receiving device 52, which indicates the start of scanning, is input into the reset circuit 94.

A clock pulse output from the clock circuit 84 is input into the motor 46 for driving the polygon mirror 44 via the motor synchronization circuit 86 to ensure synchronization with the rotation of the motor 46. The clock pulse is also input into the gate circuit 90, and passes through the gate circuit 90 only while the gate circuit 90 is opened by the edge detection circuit 88. The clock pulse that has passed through the gate circuit 90 is input into the counter 92, and a dimension of the measurement object 4 is obtained from a number of clock pulses corresponding to a length of a shadow of the measurement object 4.

Figure 2:
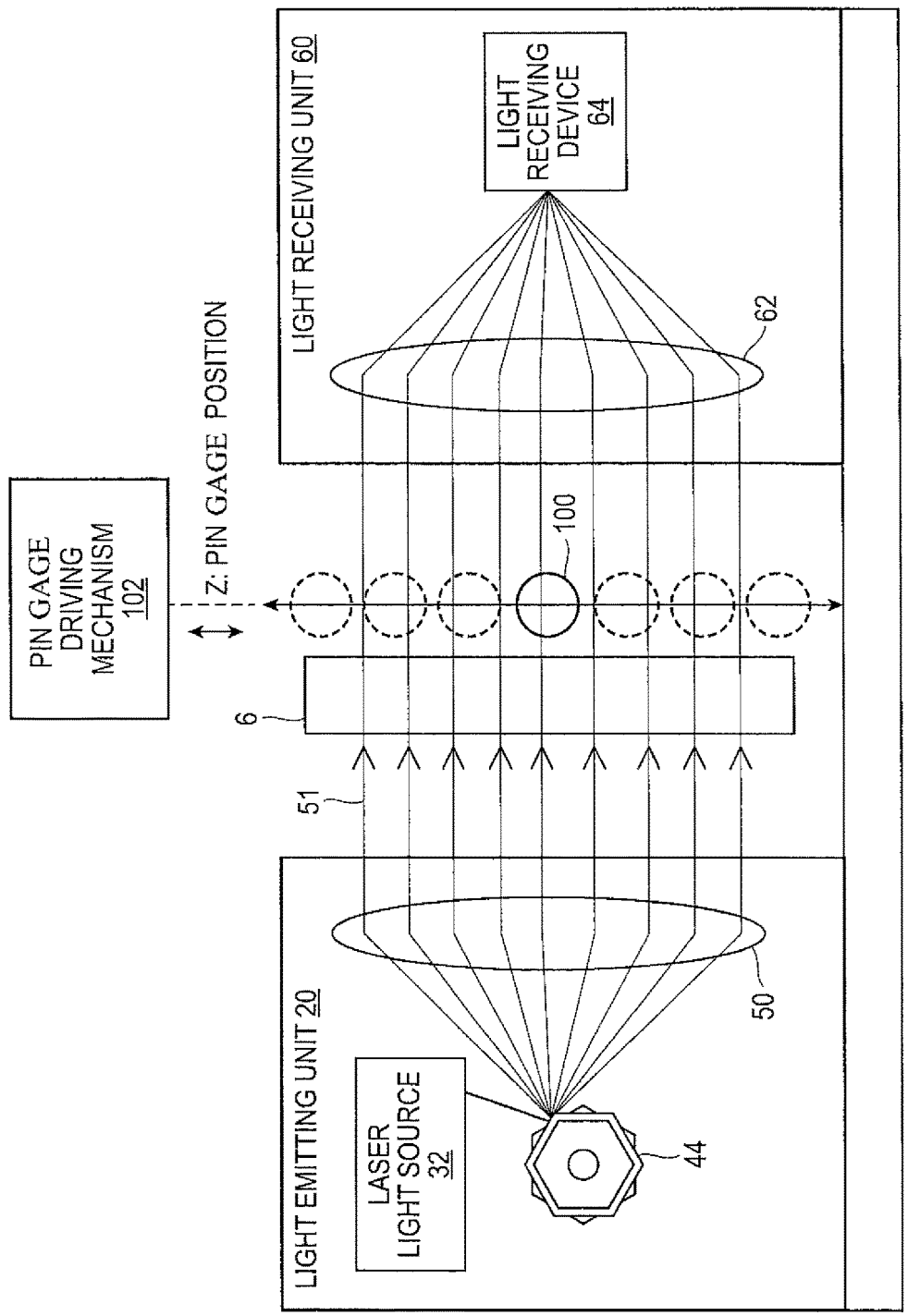
FIG. 2 is a cross-sectional view illustrating a configuration of main parts in a first embodiment.

When the disclosed embodiments are implemented using such a laser scanning-type dimension measuring apparatus, in a first embodiment, the main parts of which are schematically illustrated in FIG. 2, an object of inspection such as a glass plate (called "examined glass") 6 is disposed in the parallel scanning beam 51. Furthermore, a pin gage (also called a "plug gage") 100, for example, is disposed between the examined glass 6 and the light-receiving unit 60, and the pin gage 100 is moved parallel to a surface of the examined glass 6 by a pin gage driving mechanism 102.

Figure 3:
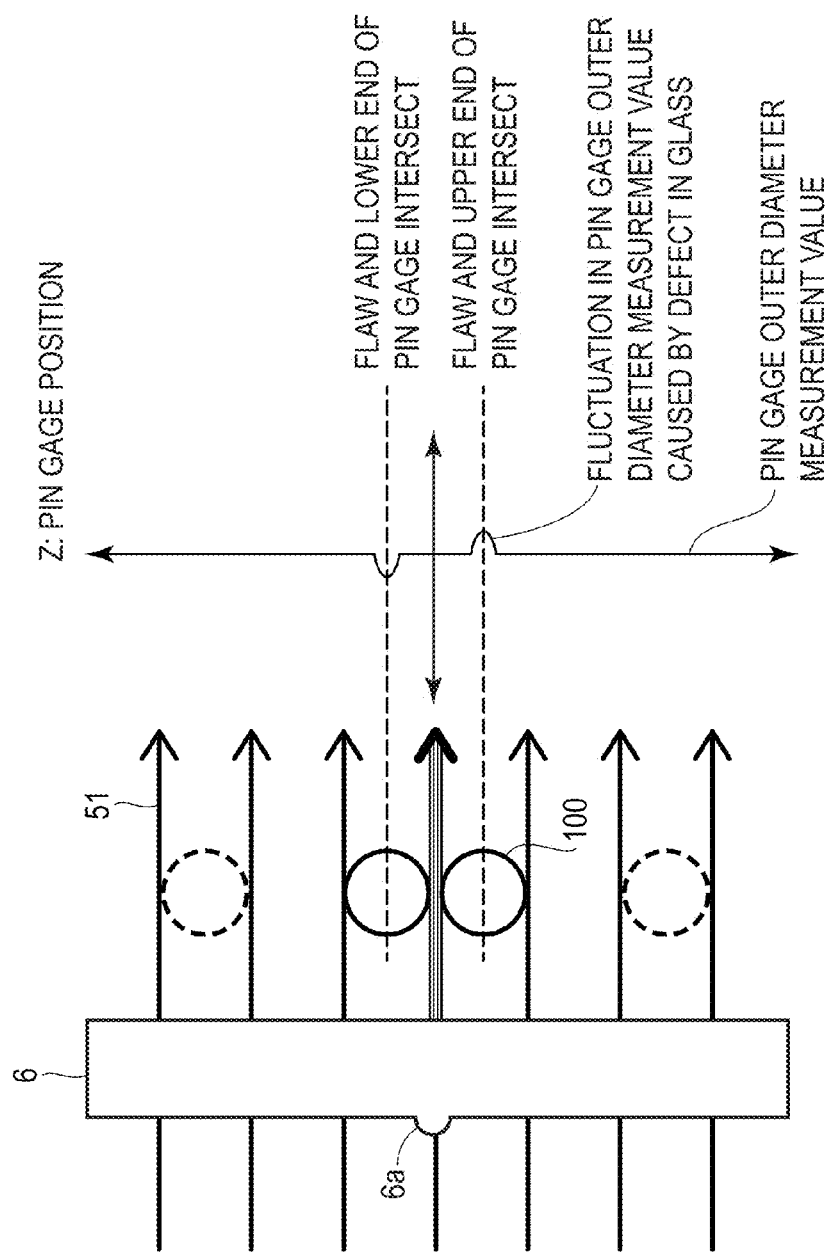
FIG. 3 is a cross-sectional view illustrating a principle of defect detection in the first embodiment.

Here, when the parallel scanning beam 51 traverses the examined glass 6, phenomena such as refraction and diffraction arise due to a defect 6a in the examined glass 6, as illustrated in FIG. 3. An outer diameter measurement value from the pin gage 100 fluctuates as a result, which makes it possible to detect the defect 6a in the examined glass 6.

Specifically, as illustrated in FIG. 3, the pin gage 100 is moved in a vertical direction, and an outer diameter measurement value of the pin gage is obtained at each of pin gage positions Z. The outer diameter measurement value fluctuates when an upper end and a lower end of the pin gage 100 intersect with the position of the defect 6a in the examined glass 6, as illustrated in FIG. 3. The presence/absence of the defect 6a in the examined glass 6 can thus be confirmed from the fluctuation in the measurement value of the pin gage outer diameter.

Figure 4A:
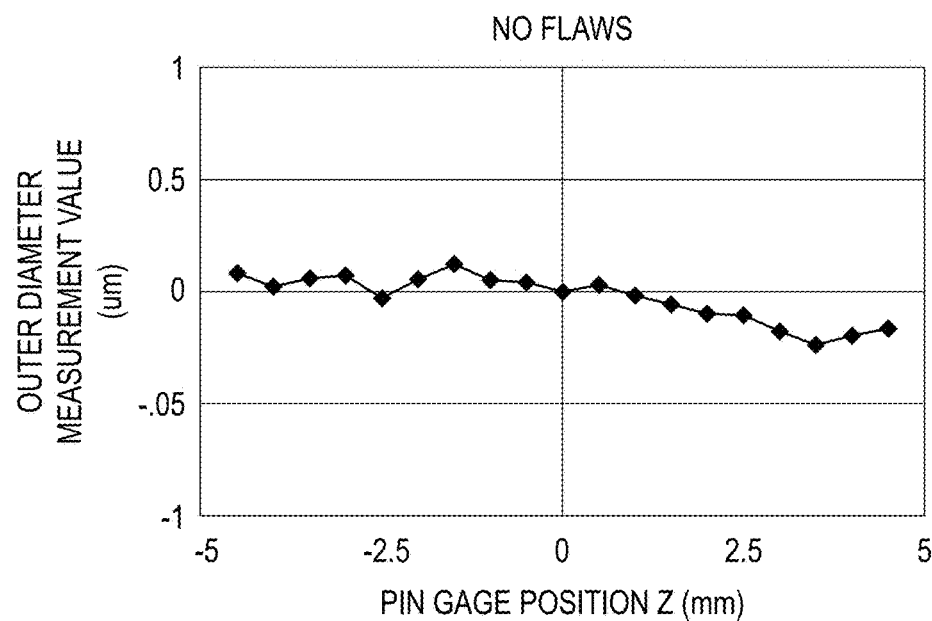
FIGS. 4A and 4B are line graphs comparing examples of fluctuations in outer diameter measurement values caused by the presence/absence of defects in the first embodiment.
Figure 4B:
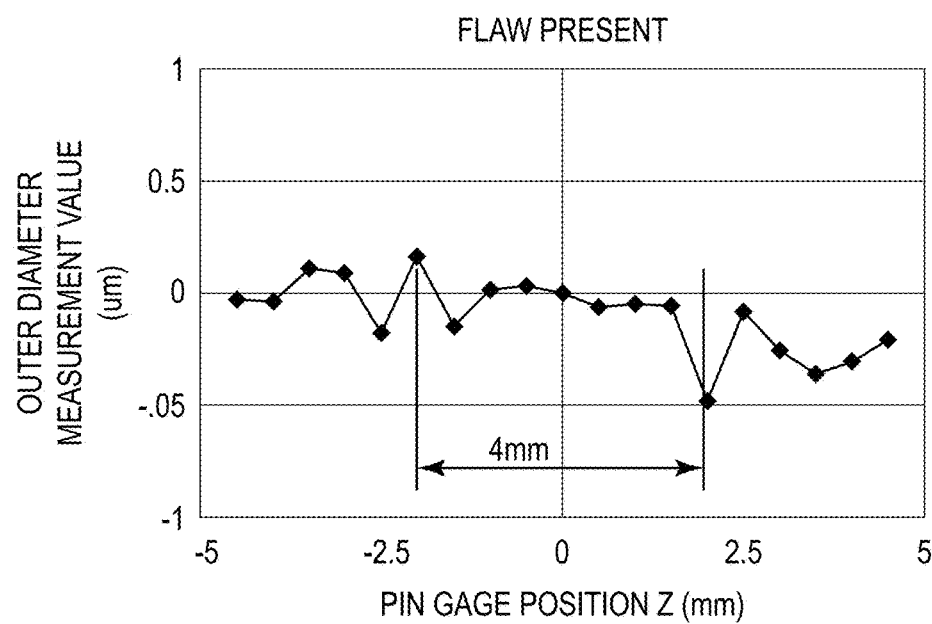

FIG. 4A illustrates an example of the fluctuation in the outer diameter measurement value of the pin gage using a 4 mm-diameter pin gage when a glass plate having no defects is arranged. On the other hand, FIG. 4B illustrates an example of the fluctuation in the outer diameter measurement value of the pin gage when a glass plate having defects is arranged. Comparing FIGS. 4A and 4B, it can clearly be seen that the outer diameter measurement value fluctuates at pin gage positions Z where a defect is present.

Figure 5:
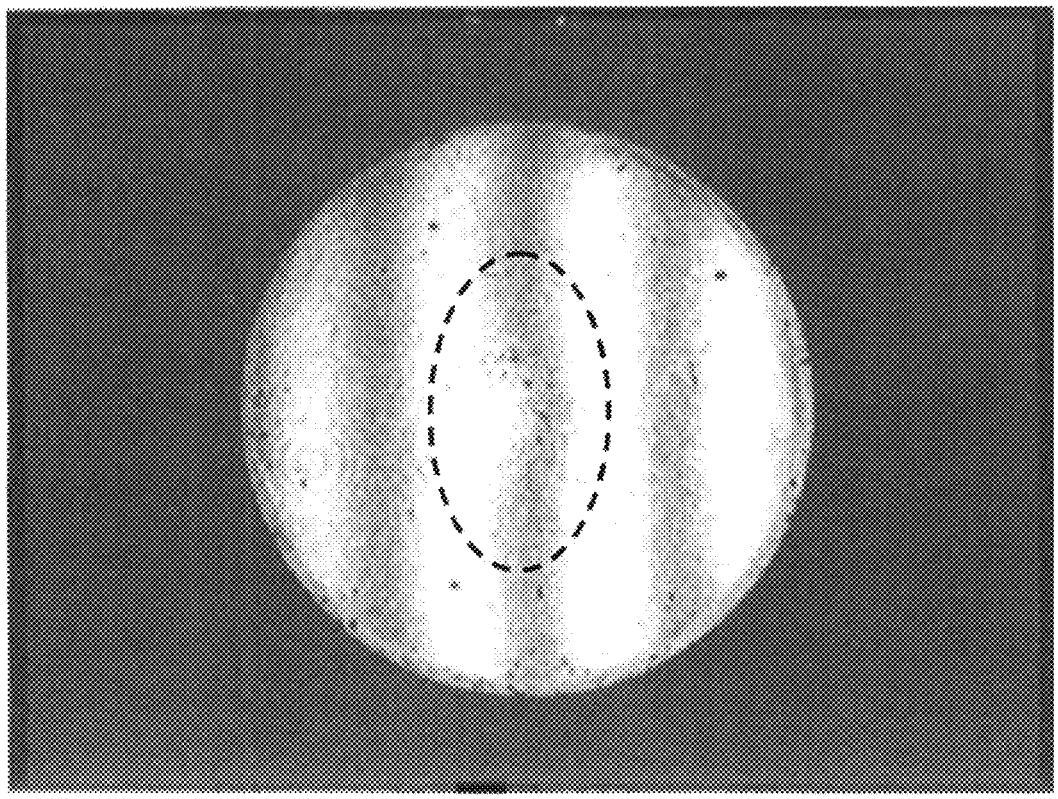
FIG. 5 is a diagram illustrating an image, observed using a laser interferometer, of an object of inspection that has defects in the first embodiment.

FIG. 5 is an image observed using a laser interferometer, corresponding to the state illustrated in FIG. 4B. From FIG. 5, it is clear that a defect is present in a central area of the glass, and that the outer diameter measurement value fluctuates at the pin gage position corresponding to that defect.

Although the foregoing embodiment describes the object of inspection as a glass plate, the embodiments are not limited to being applied thereto, and can also be applied in the examination of a lens.

Figure 6:
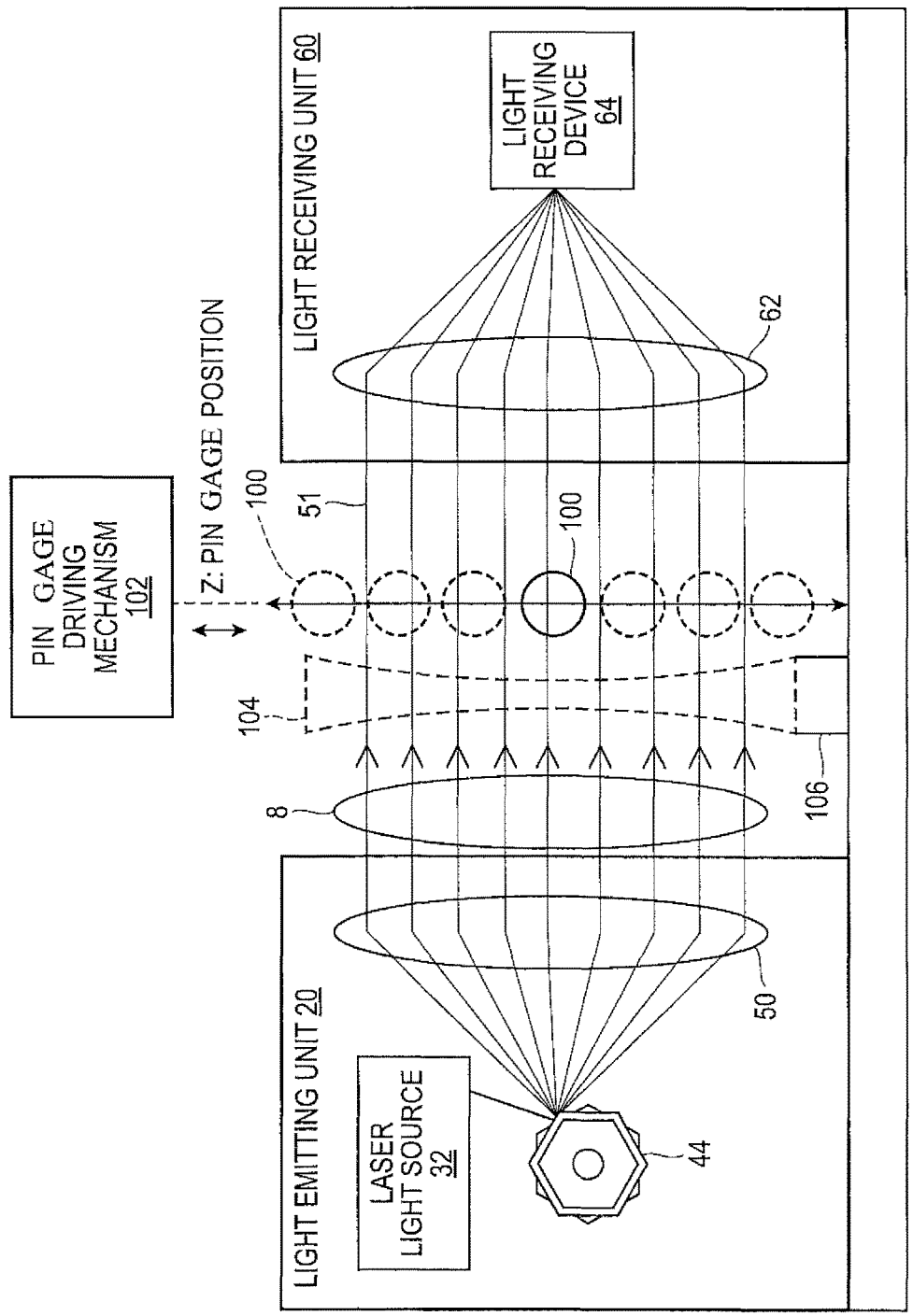
FIG. 6 is a cross-sectional view illustrating a configuration of main parts in a second embodiment.

A second embodiment which relates to the examination of a lens, is illustrated in FIG. 6. In the present embodiment, the object of inspection is assumed to be a lens such as a convex lens (called an "examined lens") 8, and an optical device 104 (because the examined lens 8 is a convex lens in the drawings, this is a concave lens that corresponds to the shape of the examined lens 8) is arranged on a mount 106 between the pin gage 100 in the parallel scanning beam 51 and the object of inspection such that the parallel scanning beam 51 traversing the examined lens 8 reaches the light receiving device 64.

The remaining configuration is the same as in the first embodiment, and thus descriptions thereof will be omitted.

By adding the optical device 104 in this manner, light traversing the examined lens 8 can be caused to reach the light receiving device 64, which makes it possible to detect defects in the same manner as in the first embodiment.

Note that in the case where the examined lens 8 is a concave lens, a convex lens can be used as the optical device 104. The optical device 104 may also be omitted depending on the shape of the lens.

Figure 7:
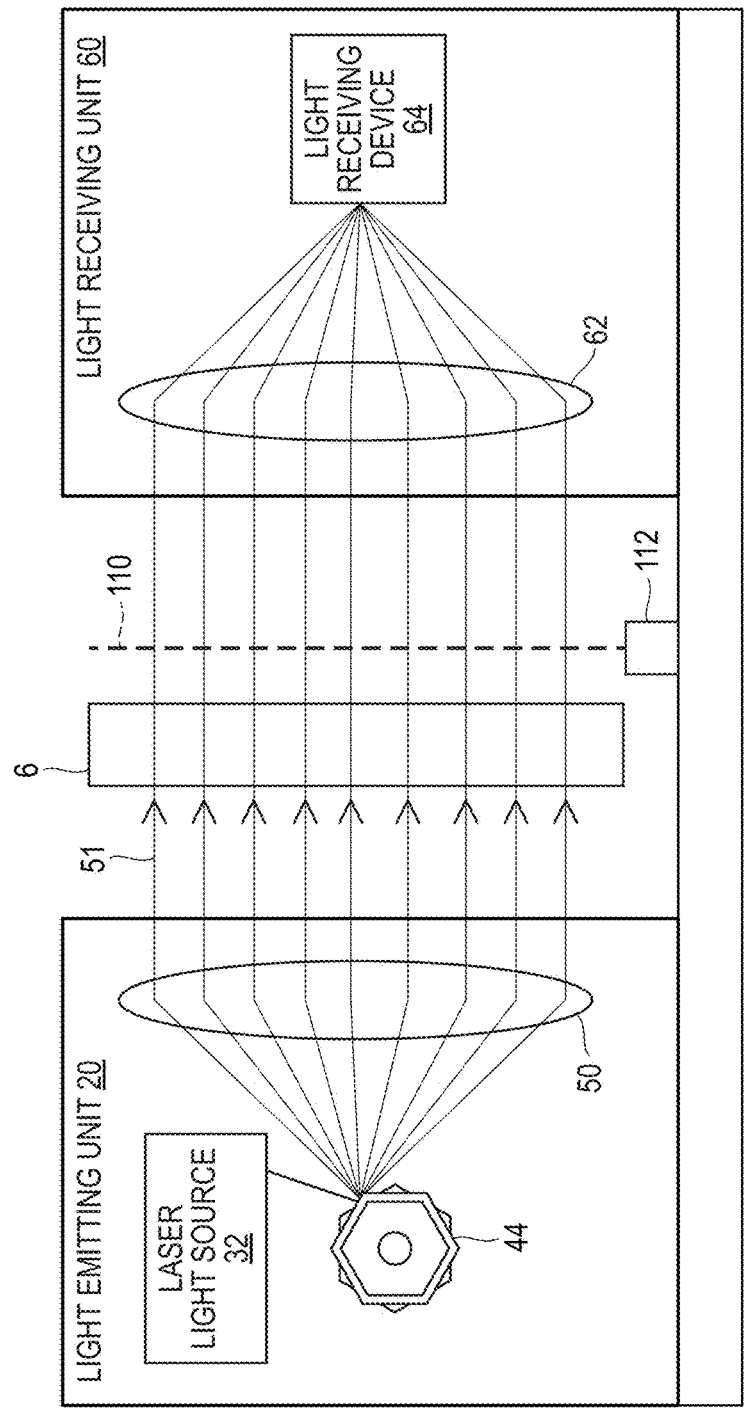
FIG. 7 is a cross-sectional view illustrating a configuration of main parts in a third embodiment.

Although the foregoing embodiments describe moving the pin gage 100 in a measurement direction (the vertical direction in the drawings), the light-blocking object is not limited to a pin gage. For example, an optical grid 110 having light and dark areas distributed at intervals smaller than a defect in the examined glass 6 can be arranged on a mount 112 and used, as in a third embodiment illustrated in FIG. 7. In this case, there is no need to move the lattice in the same manner as the pin gage, which provides a simpler configuration.

The foregoing embodiments are described as being realized using a laser scanning-type dimension measuring apparatus such as that disclosed in Japanese Patent No. 4162426B, Japanese Patent No. 4191953B, or Japanese Unexamined Patent Application Publication No. H09-138115A. However, the optical dimension measuring apparatus for realizing the disclosed embodiments is not limited thereto. For example, an image sensor-type dimension measuring apparatus such as that disclosed in Japanese Patent No. 5507879B can be applied in the same manner. As illustrated in FIG. 8, in this device, a light emitting unit 120 includes a laser light source 132 that emits fan-shaped light rays 133 and a collimator lens 150 that changes the fan-shaped light rays 133 into parallel light rays 151, and a light-receiving unit 160 includes a one-dimensional image sensor 164 such as a CCD.

In the example illustrated in FIG. 8, the light emitting unit 120 and the light-receiving unit 160 need not be integrated.

In the case where a laser scanning-type dimension measuring apparatus is used, the object of inspection is preferably from 10 to 300 mm. However, the device can also be applied when examining a large film or glass panel of approximately 1000 mm, for example.

Although the foregoing embodiments describe the object of inspection as being glass, the object of inspection is not limited thereto, and the embodiments can also be applied generally in transparent plastic.

The invention claimed is:

1. A method for detecting a defect in a transparent body, the method comprising:
    disposing a transparent body to be examined between a light emitting unit and a light-receiving unit arranged opposite each other, a light-blocking object being arranged between the transparent body and the light-receiving unit; and
    detecting a change in an optical path caused by a defect in the transparent body based on a change in a light ray emitted from the light emitting unit and being incident on the light-receiving unit after passing through the transparent body and the light-blocking object.

2. The method according to claim 1, wherein the light emitting unit scans a laser beam in a measurement direction and the light-receiving unit focuses and detects the scanned laser beam after passing through the transparent body and the light-blocking object.

3. The method according to claim 2, wherein the light-blocking object is a fixed optical lattice having light and dark areas distributed at intervals smaller than a defect in the transparent body.

4. The method according to claim 1, wherein the light emitting unit emits a linear light ray and the light-receiving unit receives the linear light ray after passing through the transparent body and the light-blocking object.

5. The method according to claim 4, wherein the light-blocking object is a pin gage that is moved in a measurement direction.

6. The method according to claim 4, wherein the light-blocking object is a fixed optical lattice having light and dark areas distributed at intervals smaller than a defect in the transparent body.

7. The method according to claim 1, wherein the light-blocking object is a pin gage that is moved in a measurement direction.

8. The method according to claim 2, wherein the light-blocking object is a pin gage that is moved in the measurement direction.

9. The method according to claim 1, wherein the light-blocking object is a fixed optical lattice having light and dark areas distributed at intervals smaller than a defect in the transparent body.

10. The method according to claim 1, wherein the transparent body is a lens.

11. A device for detecting a defect in a transparent body, the device comprising:
    a light emitting unit;

a light-receiving unit disposed opposite from the light emitting unit;

a light-blocking object disposed between the light emitting unit and the light-receiving unit; and a controller configured to detect a change in an optical path caused by a defect in a transparent body to be examined based on a change in a light ray emitted from the light emitting unit and being incident on the light-receiving unit after passing through the transparent body and the light-blocking object, wherein the device is configured to arrange the transparent body between the light emitting unit and the light-blocking object.

12. The device according to claim 11, wherein the light emitting unit includes a scanner that scans a laser beam in a measurement direction; and the light-receiving unit includes a condenser that condenses the scanned laser beam after passing through the transparent body and the light-blocking object.

13. The device according to claim 12, wherein the light-blocking object is a pin gage that moves in the measurement direction.

14. The device according to claim 12, wherein the light-blocking object is a fixed optical lattice having light and dark areas distributed at intervals smaller than a defect in the transparent body.

15. The device according to claim 11, wherein the light emitting unit includes an emitter that emits a linear light ray; and the light-receiving unit includes a receiver that receives the linear light ray after passing through the transparent body and the light-blocking object.

16. The device according to claim 15, wherein the light-blocking object is a pin gage that moves in a measurement direction.

17. The device according to claim 15, wherein the light-blocking object is a fixed optical lattice having light and dark areas distributed at intervals smaller than a defect in the transparent body.

18. The device according to claim 11, wherein the light-blocking object is a pin gage that moves in a measurement direction.

19. The device according to claim 11, wherein the light-blocking object is a fixed optical lattice having light and dark areas distributed at intervals smaller than a defect in the transparent body.

20. The device according to claim 11, wherein the device includes an optical element having a shape corresponding to the shape of a lens when the transparent body is the lens.

* * * * *